(12) United States Patent
Sondgeroth et al.

(10) Patent No.: US 8,388,991 B2
(45) Date of Patent: Mar. 5, 2013

(54) MOISTURIZING ANTIMICROBIAL COMPOSITION

(75) Inventors: Jason Sondgeroth, Ooltewah, TN (US); Joe Czerwinkski, Signal Mt, TN (US)

(73) Assignee: Chattem, Inc., Chattanooga, TN (US)

( * ) Notice: Subject to any disclaimer, the term of this patent is extended or adjusted under 35 U.S.C. 154(b) by 226 days.

(21) Appl. No.: 12/771,080

(22) Filed: Apr. 30, 2010

(65) Prior Publication Data

US 2010/0278906 A1 Nov. 4, 2010

Related U.S. Application Data

(60) Provisional application No. 61/174,724, filed on May 1, 2009.

(51) Int. Cl.
*A01N 25/00* (2006.01)
*A01N 33/12* (2006.01)
*A61K 8/02* (2006.01)
*A61K 9/127* (2006.01)
*A61K 33/02* (2006.01)

(52) U.S. Cl. ........ 424/405; 424/401; 424/450; 514/642; 514/828; 514/643

(58) Field of Classification Search ........................ None
See application file for complete search history.

(56) References Cited

U.S. PATENT DOCUMENTS

| | | | |
|---|---|---|---|
| 3,247,119 A | 4/1966 | Herrick et al. | |
| 3,968,246 A | 7/1976 | Merianos et al. | |
| 4,336,152 A | 6/1982 | Like et al. | |
| 4,797,420 A | 1/1989 | Bryant | |
| 4,818,271 A | 4/1989 | Henrie, II | |
| 4,822,601 A | 4/1989 | Goode et al. | |
| 5,063,062 A | 11/1991 | Greenspan et al. | |
| 5,284,833 A | 2/1994 | McAnalley et al. | |
| 5,661,170 A | 8/1997 | Chodosh | |
| 5,720,961 A | 2/1998 | Fowler et al. | |
| 5,767,163 A | 6/1998 | Kundsin | |
| 5,880,076 A | 3/1999 | Vermeer | |
| 6,238,678 B1 | 5/2001 | Oblong et al. | |
| 6,248,343 B1 | 6/2001 | Jampani et al. | |
| 6,294,186 B1 | 9/2001 | Beerse et al. | |
| 6,383,505 B1 | 5/2002 | Kaiser et al. | |
| 6,436,442 B1 | 8/2002 | Woo et al. | |
| 6,534,069 B1 | 3/2003 | Asmus et al. | |
| 6,846,846 B2 | 1/2005 | Modak et al. | |
| 6,958,148 B1 | 10/2005 | Green et al. | |
| 7,175,836 B1 | 2/2007 | Hart et al. | |
| 7,192,601 B2 | 3/2007 | Walker | |
| 7,201,914 B2 | 4/2007 | Dees | |
| 7,217,424 B2 | 5/2007 | Pereira et al. | |
| 7,348,018 B2 | 3/2008 | McAtee et al. | |
| 2002/0022660 A1* | 2/2002 | Jampani et al. ............... 514/635 |
| 2002/0086039 A1 | 7/2002 | Lee et al. | |
| 2002/0098159 A1 | 7/2002 | Wei et al. | |
| 2003/0165546 A1 | 9/2003 | Resch et al. | |
| 2004/0132667 A1 | 7/2004 | Lintner | |
| 2004/0138088 A1 | 7/2004 | Pereira et al. | |
| 2004/0166183 A1 | 8/2004 | Ruseler-van Embden et al. |
| 2004/0191191 A1 | 9/2004 | Ehlis et al. | |
| 2004/0247685 A1 | 12/2004 | Modak et al. | |
| 2005/0020468 A1 | 1/2005 | Frantz et al. | |
| 2005/0037040 A1 | 2/2005 | Arkin et al. | |
| 2005/0175554 A1 | 8/2005 | Wagner et al. | |
| 2005/0196360 A1 | 9/2005 | Comte et al. | |
| 2005/0203026 A1 | 9/2005 | Day et al. | |
| 2005/0232894 A1 | 10/2005 | Weiner et al. | |
| 2006/0018867 A1 | 1/2006 | Kawasaki et al. | |
| 2006/0104940 A1 | 5/2006 | Heinrichs et al. | |
| 2006/0135627 A1 | 6/2006 | Frantz et al. | |
| 2006/0153783 A1 | 7/2006 | Ehlis et al. | |
| 2006/0188459 A1 | 8/2006 | Heinrichs et al. | |
| 2006/0193813 A1 | 8/2006 | Simonnet | |
| 2006/0235084 A1 | 10/2006 | Heller et al. | |
| 2006/0235161 A1 | 10/2006 | Heller et al. | |
| 2007/0027050 A1 | 2/2007 | Crotty et al. | |
| 2007/0048235 A1 | 3/2007 | Harmalker et al. | |
| 2007/0066499 A1 | 3/2007 | Slavtcheff et al. | |
| 2007/0138674 A1 | 6/2007 | Anastasiou et al. | |
| 2007/0202069 A1 | 8/2007 | Tamareselvy et al. | |
| 2007/0292358 A1 | 12/2007 | Emmerling et al. | |
| 2008/0081052 A1 | 4/2008 | Zhang | |
| 2008/0159970 A1 | 7/2008 | Willemin | |
| 2008/0226706 A1 | 9/2008 | Kumar | |
| 2008/0247985 A1 | 10/2008 | Zhang | |
| 2008/0287514 A1 | 11/2008 | Zhang | |
| 2008/0287515 A1 | 11/2008 | Zhang | |
| 2008/0293825 A1 | 11/2008 | Littau et al. | |
| 2008/0299157 A1 | 12/2008 | Fares et al. | |
| 2008/0312304 A1 | 12/2008 | Zhang | |
| 2009/0004122 A1 | 1/2009 | Modak et al. | |

(Continued)

FOREIGN PATENT DOCUMENTS

| | | |
|---|---|---|
| EP | 1011630 A1 | 6/2000 |
| EP | 1465584 A1 | 10/2004 |

(Continued)

OTHER PUBLICATIONS http://www.personalcaremagazine.com/Print.aspx?Story=1509, published in 2006, Author: Alan Park, et al., No Volume, No Number. pp. 1-4.*

(Continued)

*Primary Examiner* — Robert M Kelly
(74) *Attorney, Agent, or Firm* — Husch Blackwell LLP

(57) ABSTRACT

An antimicrobial moisturizing composition includes benzethonium chloride or benzalkonium chloride, a non-benzyl cationic surfactant, and an aqueous carrier. The composition of the present invention provides a significant and unexpected reduction of irritation, inflammation, dryness and/or redness, all issues associated with known alcohol-based skin disinfectants. In particular, the present invention provides a stable, aesthetically-pleasing, long-lasting, and moisturizing antimicrobial composition that is substantially free of ethanol, polysorbates, and anionic compounds that are known to inhibit the activity of benzethonium chloride or benzalkonium chloride.

12 Claims, No Drawings

U.S. PATENT DOCUMENTS

| | | |
|---|---|---|
| 2009/0035236 A1 | 2/2009 | Maes et al. |
| 2009/0035237 A1 | 2/2009 | Maes et al. |
| 2009/0035240 A1 | 2/2009 | Maes et al. |
| 2009/0035242 A1 | 2/2009 | Maes et al. |
| 2010/0234328 A1* | 9/2010 | Ahmed et al. ............ 514/159 |

FOREIGN PATENT DOCUMENTS

| | | | |
|---|---|---|---|
| EP | 1665933 | A2 | 6/2006 |
| EP | 1581568 | B1 | 7/2006 |
| EP | 1702608 | A1 | 9/2006 |
| EP | 1702609 | A1 | 9/2006 |
| EP | 1702610 | A1 | 9/2006 |
| EP | 1779893 | A1 | 5/2007 |
| EP | 1820396 | A1 | 8/2007 |
| EP | 1870086 | A1 | 12/2007 |
| EP | 1958613 | A1 | 8/2008 |
| EP | 1972330 | A2 | 9/2008 |
| FR | 2891456 | A1 | 4/2007 |
| GB | 1250219 | A | 10/1971 |
| GB | 2409203 | A | 6/2005 |
| GB | 2414666 | A | 12/2005 |
| GB | 2440638 | A | 2/2008 |
| GB | 2445635 | A | 7/2008 |
| WO | 9848768 | A1 | 11/1998 |
| WO | 9850005 | A1 | 11/1998 |
| WO | 9945771 | A1 | 9/1999 |
| WO | 0106829 | A2 | 2/2001 |
| WO | 0107009 | A1 | 2/2001 |
| WO | 02078667 | A1 | 10/2002 |
| WO | 2006062846 | A2 | 6/2006 |
| WO | 2007070643 | A2 | 6/2007 |
| WO | 2007095008 | A2 | 8/2007 |
| WO | 2008019213 | A2 | 2/2008 |
| WO | 2008035246 | A2 | 3/2008 |
| WO | 2008079898 | A1 | 7/2008 |
| WO | 2008134712 | A2 | 11/2008 |

OTHER PUBLICATIONS

Lonzagard(TM): The Choice of Active Ingredients for Antimicrobial Formulations, Aug. 2002, Lonza Inc, USA.

Benzethonium Chloride USP, Lonza Inc, USA, (2002).

Lonzagard(TM) Benzethonium Chloride USP for Personal Care Applications, Lonza Inc, USA, (2003).

David L. Dyer, PhD; Arnold Shinder, DO; Fay Shinder, RN; Alcohol-free Instant Hand Sanitizer Reduces Elementary School Absenteeism, Family Medicine, Oct. 2000, pp. 633-638, vol. 32, No. 9.

David L. Dyer; Kenneth B. Gerenraich; Peter S. Wadhams; Testing a New Alcohol-Free Hand Sanitizer to Combat Infection, AORN Journal, Aug. 1998, pp. 239-251, vol. 68, No. 2.

MSDS—Material Data Safety Sheet, Product Name: Dermal Defense—Lotionized Non Alcohol Hand Sanitizer, Oct. 22, 2003, MSDS No. 038201.

DermalDefense(TM) Professional Hand Hygiene Products Antimicrobial Hand Sanitizer Lotion pamphlet, Tri-anim, (2000).

* cited by examiner

MOISTURIZING ANTIMICROBIAL COMPOSITION

CROSS-REFERENCE TO RELATED APPLICATIONS

This application is a nonprovisional of and claims priority to U.S. Provisional Application No. 61/174,724, filed May 1, 2009, which document is hereby incorporated by reference in its entirety to the extent permitted by law.

BACKGROUND OF THE INVENTION

A significant cause of many illnesses has long been known to involve the transmission through skin contact of bacteria, germs, microorganisms, viruses and other deleterious substances. From sniffing coworkers to raw chicken on a kitchen cutting board, every day life is full of potential infectious disease hazards. Infectious diseases typically spread through two types of contact. With direct contact, infectious disease can be spread in three different ways. The most common way for infectious disease to spread is through the direct transfer of bacteria, viruses or other germs from one person to another. This can occur when an individual with the bacterium or virus touches or coughs on someone who is not infected. These germs can also spread through the exchange of body fluids from sexual contact or a blood transfusion.

Many household pets also carry a variety of germs. Being bitten or scratched by an infected animal can make a person sick and, in extreme circumstances, could even cause death. Handling animal waste can be hazardous, too. In a third type of direct contact, a pregnant woman may pass germs that cause infectious diseases to her unborn baby. Germs can pass through the placenta, as is the case of the AIDS virus and the toxoplasmosis parasite. Or germs could spread during labor and delivery, as is the case for a mother infected with group B streptococcus.

Disease-causing organisms can also be passed along by indirect contact. Many germs can linger on an inanimate object, such as a tabletop, doorknob or faucet handle. When a person touches the same doorknob grasped by someone ill with the flu or a cold, for example, it is possible to pick up the genus the infected person left behind. By subsequently touching one's eyes, mouth or nose, the uninfected person may become infected. Some infections occur from organisms that naturally live in the environment but are not passed from person to person. Examples include fungal infections like histoplasmosis or blastomycosis, as well as bacterial infections such as anthrax.

Infectious diseases can also spread through the air. For example, when a person coughs or sneezes, droplets are expelled into the air. When that person is sick with a cold or the flu—or any number of other illnesses—these droplets contain the germ-causing illness. Spread of infectious disease in this manner is called droplet spread or droplet transmission. Droplets travel only about three feet because they're usually too large to stay suspended in the air for a long time. However, if a droplet from an infected person comes in contact with your eyes, nose or mouth, you may soon experience symptoms of the illness. Crowded, indoor environments may promote the chances of droplet transmission—which may explain the increase in respiratory infections in the winter months.

Some disease-causing germs travel through the air in particles considerably smaller than droplets. These tiny particles remain suspended in the air for extended periods of time and can travel in air currents. If you breathe in an airborne virus, bacterium or other germ, you may become infected and show signs and symptoms of the disease. Colds caused by viruses, influenza and tuberculosis are a few types of infectious diseases usually spread through the air, in both particle and droplet forms.

Some germs rely on insect carriers—such as mosquitoes, fleas, lice or ticks—to move from host to host. These carriers are known as vectors. Mosquitoes can carry the malaria parasite or West Nile virus, and deer ticks may carry the bacterium that causes Lyme disease.

The vector-borne spread of germs happens when an insect that carries the germ on its body or in its intestinal tract lands on you or bites you. The germs move into your body and can make you sick. Sometimes the germs that cause infectious disease need the insect for specific biological reasons. They use the insect's body to multiply, which is necessary before the germs can infect a new host.

Another way disease-causing germs can infect you is through contaminated food and water. Sometimes called common-vehicle transmission, this mechanism of transmission allows germs to be spread to many people through a single source. Food is often the vehicle that spreads the germs and causes the illness. For instance, contamination with *Escherichia coli* (*E. coli*) is common. *E. coli* is a bacterium present in or on certain foods—such as undercooked hamburger or unwashed fruits or vegetables. When you eat foods contaminated with *E. coli*, chances are you'll experience an illness—sometimes referred to as food poisoning.

According to many experts, including the Centers for Disease Control, hand washing is the single most effective way to prevent the spread of infectious diseases. However, when the convenience of soap and water is not readily available, hand washing may not be an option. Skin disinfectants that do not require the application of water have therefore been developed in response to the need for a skin disinfectant that is effective and easy to use. However, many of these skin disinfectants use alcohol as the primary antimicrobial agent. This is problematic because the effective concentration of alcohol, especially ethanol, generally believed to about greater than about 60% by weight, is irritating to the skin and can cause dryness with resultant peeling and cracking. Because chapped skin tends to be more susceptible to microbial contamination, repeated use of alcohol disinfectants can exacerbate the very problem they are intended to solve. Benzethonium chloride has also been used in known skin disinfectants. However, the antimicrobial activity of benzethonium chloride is easily inhibited by polysorbates and anionics that are commonly used in skin disinfectant formulations. There is therefore a need in the art for an antimicrobial composition that is effective as a skin disinfectant but does not cause increased irritation to the skin of the average user.

SUMMARY OF THE INVENTION

In one of many illustrative aspects of the present invention, there is provided an improved antimicrobial moisturizing composition, the improved composition including purified water, benzethonium chloride or benzalkonium chloride, and a cationic surfactant.

In another illustrative aspect of the present invention there is provided a method of making the improved composition of the present invention.

In yet another illustrative aspect of the present invention there is provided a method of topically administering to an affected area a non-toxic effective dosage of the improved composition.

DETAILED DESCRIPTION OF THE INVENTION

The present invention is generally directed to a moisturizing antimicrobial composition and its use. In particular, the present invention provides a novel combination of benzethonium chloride or benzalkonium chloride or mixtures thereof, a cationic surfactant, and an aqueous carrier. The resulting composition provides a significant and unexpected reduction of irritation, inflammation, dryness and/or redness, all issues associated with known alcohol-based skin disinfectants. In particular, the present invention is generally directed to a stable, aesthetically-pleasing, long-lasting, and moisturizing antimicrobial composition comprising benzethonium chloride or benzalkonium chloride that is substantially free of ethanol, polysorbates (polyethylene glycol sorbitan fatty esters), and anionic compounds that are known to inhibit the activity of benzethonium chloride or benzalkonium chloride.

The composition of the present invention generally has a viscosity of from about 10,000 to about 1,000,000 centipoise. In certain embodiments, the viscosity of the composition may be from about 100,000 to about 200,000 centipoise and, in other embodiments wherein a sheer formula is desirable, the viscosity of the composition may be from about 30,000 to about 50,000 centipoise The composition hereof includes from about from about 0.05% to about 4%, more preferably from about 0.1% to about 0.5%, and most preferably from about 0.10% to 0.20% by weight of benzethonium chloride, benzalkonium chloride, mixtures and derivatives thereof. Benzethonium chloride is a synthetic quaternary ammonium salt. This compound is an odorless white solid; soluble in water. It has surfactant, antiseptic, and anti-infective properties, and it is used as a topical antimicrobial agent in first aid antiseptics. It is also found in cosmetics and toiletries such as mouthwashes (disguised as grapefruit seed extract; see below), anti-itch ointments, and antibacterial moist towelettes. Benzethonium chloride is also used in the food industry as a hard surface disinfectant. In addition to its highly effective antimicrobial activity, benzethonium chloride contains a positively charged nitrogen atom covalently bonded to four carbon atoms. This positive charge attracts it to the skin and hair. This contributes to a soft, powdery after feel on the skin and hair, as well as long-lasting persistent activity against microorganisms. Benzethonium chloride exhibits a broad spectrum of microbiocidal activity against bacteria, fungi, mold and viruses such as, for example, MRSA, VISA, *Salmonella, E. coli*, C. diff, Hepatitis B and C, Herpes, HIV, RSV, and Norovirus.

Benzalkonium chloride, also known as alkyldimethylbenzylammonium chloride and ADBAC, is a mixture of alkylbenzyldimethylammonium chlorides of various even-numbered alkyl chain lengths. This product is a nitrogenous cationic surface-acting agent belonging to the quaternary ammonium group. It has three main categories of use; as a biocide, a cationic surfactant and phase transfer agent in the chemical industry. Benzalkonium chloride is readily soluble in ethanol and acetone. Although dissolution in water is slow, aqueous solutions are easier to handle and are preferred. Solutions should be neutral to slightly alkaline, with color ranging from clear to a pale yellow. Solutions foam profusely when shaken, have a bitter taste and a faint almond-like odor which is only detectable in concentrated solutions.

The greatest biocidal activity is associated with the C12-C14 alkyl derivatives. The mechanism of bactericidal/microbicidal action is thought to be due to disruption of intermolecular interactions. This can cause dissociation of cellular membrane lipid bilayers, which compromises cellular permeability controls and induces leakage of cellular contents. Other biomolecular complexes within the bacterial cell can also undergo dissociation. Enzymes, which finely control a wide range of respiratory and metabolic cellular activities, are particularly susceptible to deactivation. Critical intermolecular interactions and tertiary structures in such highly specific biochemical systems can be readily disrupted by cationic surfactants.

Benzalkonium chloride solutions are rapidly acting biocidal agents with a moderately long duration of action. They are active against bacteria and some viruses, fungi, and protozoa. Bacterial spores are considered to be resistant. Solutions are bacteriostatic or bactericidal according to their concentration. Gram-positive bacteria are generally more susceptible than Gram-negative.

Benzalkonium blended with various quaternary ammonium derivatives can be used to extend the biocidal spectrum and enhance the efficacy of benzalkonium based disinfection products. This technique has been used to improve virucidal activity of quaternary ammonium-based formulations to healthcare infection hazards such as hepatitis, HIV, etc. However, formulation requires great care as benzalkonium solutions can be readily inactivated in the presence of organic and inorganic contamination. Solutions are incompatible with soaps, and must not be mixed with anionic surfactants. Hard water salts can also reduce biocidal activity.

Surfactants reduce the surface tension of water by absorbing at the liquid-gas interface. They also reduce the interfacial tension between oil and water by adsorbing at the liquid-liquid interface. Many surfactants can also assemble in the bulk solution into aggregates. Examples of such aggregates are vesicles and micelles. The concentration at which surfactants begin to form micelles is known as the critical micelle concentration or CMC. When micelles form in water, their tails form a core that can encapsulate an oil droplet, and their (ionic/polar) heads form an outer shell that maintains favorable contact with water. When surfactants assemble in oil, the aggregate is referred to as a reverse micelle. In a reverse micelle, the heads are in the core and the tails maintain favorable contact with oil. Surfactants are also often classified into four primary groups; anionic, cationic, non-ionic, and zwitterionic (dual charge).

In the present invention, cationic surfactants wherein the head is positively charged are particularly preferred in order to contribute to the disinfecting and sanitizing properties of the composition. The composition of the present invention generally includes from about 0.01% to about 10% by weight, more preferably from about 0.1% to about 4% by weight, and most preferably from about 0.5% to about 1.5% by weight of a cationic surfactant. While not required, particularly preferred for use in the present invention are water-soluble, organic, non-benzyl cationic surfactants having a charge density of greater than about 1.3 meq/g and a molar mass of less than about 800 g/mol. Suitable cationic surfactants may include, but are not limited to, fatty quaternary amines such as alkyl ammonium chlorides, dimethyl dialkyl ammonium chlorides, alkyl ammonium methosulfates, and alkyl ammonium chlorides; behentrimonium methosulfate; distearyl dimonium chloride; laurtrimonium chloride; lauralkonium chloride; olealkonium chloride; dilauryldimonium chloride; cetalkonium chloride; dicetyldimonium chloride; laurylpyridinium chloride; cetylpyridinium chloride; soyatrimonium chloride; cetrimonium chloride; mytrimonium chloride; stearamidoethylethanolamine; stearamidoethyldiethanolamine; isostearamidopropylmorpholine; stearamidopropylmorpholine; stearamidopropyldimethylamine; diethylaminoethyl stearamide; dimethylaminopropyl myristamine; cetethyldimonium bromide; cetrimonium tosylate; stearalkonium chloride; cetrimonium bromide; cetethylmorpholinium ethosulfate; behenalkonium chloride; behentrimonium chloride; mytrimonium bromide; derivatives and combinations thereof; and acid-neutralized amidoamines such as alkyl amidopropyl dimethylamine, alkyl amidoethylethanolamine, iso alkyl amidoproylmorpholine, alkyl amidopropylmorpholine, alkyl amidopropyldimethylamine, derivatives and combinations thereof. However, it will be appreciated by those skilled in the art that cationic surfactants having a molar mass of greater than 800 g/mol may also be used if suitable including, for example, polyacrylate-1 crosspolymer.

As used herein, surfactants may also include emulsifiers such as non-ionic or cationic self-emulsifying waxes that are preferably soluble in alcohol at ambient temperature including Incroquat Behenyl TMS, Incroquat Behenyl TMS-50, stearyl alcohol and cetearyl alcohol. Non-limiting emulsifiers can also include, but are not limited to, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. In certain embodiments, preferred emulsifiers include soya sterol, cetyl alcohol, stearic acid, emulsifying wax, acrylates, silicone-containing emulsifiers and mixtures thereof. Other specific emulsifiers that can be used in the composition of the present invention include, but are not limited to, one or more of the following: $C_{10-30}$ alkyl acrylate crosspolymer; Dimethicone PEG-7 isostearate, acrylamide copolymer; mineral oil; sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; steareth-2, steareth-10, steareth-20, steareth-21 and combinations thereof.

The composition of the present invention further includes from about 30% to 90%, preferably 40% to 80%, and most preferably from 50% to 60% by weight of an aqueous carrier such as water. Water is preferably distilled or deionized water having a neutral pH. In an illustrative example, a suitable carrier is formulated, as is well known in the art, after which the active ingredients are added. The carrier may be aqueous and the composition may take the form of emulsions, creams, lotions, ointments, serums, liquids, lacquers, gels, sprays, exfoliating particulates, cleansing agents, cosmetics agents, bath additives, oils, nanosized particulates or liposomes, fragrances, powders, muds, masks, and combinations thereof.

In certain non-limiting embodiments of the present invention, the composition hereof may be in the form of an oil-in-water-type or water-in-oil-type emulsion product containing a large amount of water and/or a polyol and having high water-retaining qualities and long-term stability. In the present invention, the term "polyol" means glycerin and polymers thereof; glycols such as polyethylene glycol, propylene glycol, and 1,3-butylene glycol; and saccharides such as xylitol, sorbitol, and maltitol. In addition, the composition hereof can hold not only water but also aqueous solutions dissolving, for example, inorganic salts, organic salts, water-soluble agents, or animal or plant extracts therein. Specifically, examples of the inorganic salts include sodium chloride, potassium chloride, calcium chloride, magnesium chloride, sodium sulfate, magnesium sulfate, sodium carbonate, sodium hydrogen carbonate, and sodium phosphate. Examples of the organic salts include sodium citrate, sodium malate, sodium gluconate, sodium lactate, sodium succinate, and sodium tartrate. Examples of the water-soluble agents include skin-lightening agents. Examples of the skin-lightening agents include ascorbic acid and/or derivatives thereof, such as L-ascorbic acid glucoside, L-ascorbic acid-2-phosphate ester, L-ascorbic acid-3-phosphate ester, L-ascorbic acid-6-phosphate ester, L-ascorbic acid-2-polyphosphate ester, L-ascorbic acid-2-sulfate ester, L-ascorbic acid-2-palmitate ester, L-ascorbic acid-6-palmitate ester, L-ascorbic acid-2-stearate ester, L-ascorbic acid-6-stearate ester, L-ascorbic acid-2,6-dibutyl ester, L-ascorbic acid-2,6-dipalmitate ester, and salts thereof. Examples of the salts include sodium salts, potassium salts, magnesium salts, calcium salts, barium salts, ammonium salts, monoethanolamine salts, diethanolamine salts, triethanolamine salts, monoisopropanolamine salts, and triisopropanolamine salts. Other examples of the skin-lightening agent include arbutin, kojic acid, and glutathione. Examples of water-soluble agents include anti-inflammatory agents. Examples of the anti-inflammatory agents include glycyrrhizinic acid derivatives and allantoin.

Examples of suitable animal or plant extracts include Nettle leaf extract, Siberian ginseng extract, Phellodendron bark extract, *Coffea Arabica* extract, White birch extract, *Mentha piperita* extract, *Thymus* extract, Tea extract, *Hamamelis* extract, *Isodonis japonica* extract, Coltsfoot extract, *Vitis vinifera* leaf extract, *Humulus lupulus* extract, Horse chestnut extract, *Melissa officinalis* extract, Acerola extract, Rose fruit extract, *Actinidia chinensis* fruit extract, *Arnica* extract, *Scutellaria baicalensis* root extract, *Coptis rhizome* extract, *Lamium album* extract, Cattail extract, *Chamomilla recutita* extract, *Artemisia capillaris* flower extract, *Glycyrrhiza glabra* extract, *Gardenia florida* extract, *Sasa veitchii* extract, *Gentiana* extract, *Clammellia sinensis* extract, *Symphytum officinale* leaf extract, *Perilla ocymoides* leaf extract, *Lithospermum erythrorhizone* root extract, Linden extract, *Spiraea ulmaria* extract, *Paeonia albiflora* root extract, *Lonicera japonica* extract, *Salvia officinalis* extract, *Hedera helix* extract, *Sambucus nigra* flower extract, *Achillea millefolium* extract, *Swertia japonica* extract, Mulberry root extract, *Calendula officinalis* flower extract, *Eriobotrya japonica* leaf extract, *Prunus persica* leaf extract, *Centaurea cyanus* flower extract, *Saxifrage sarmentosa* extract, Mogwort extract, *Lactuca scariola* sativa extract, *Anthemis nobilis* flower extract, and *Sanguisorba officinalis* root extract. In the present invention, the above-mentioned inorganic salts, organic salts, water-soluble agents, and animal or plant extracts may be used alone or in a combination of two or more thereof.

If desired, the composition may further include one or more neutralizers, such as, for example, strong and weak bases. Any suitable neutralizer can be selected, as will be appreciated by one of ordinary skill in the art. Exemplary neutralizers suitable for use in the compositions of the present invention included sodium hydroxide, potassium hydroxide, ammonium hydroxide, diethanolamine, triethanolamine, 2-dimethylamino-2-methyl-1-propanol (DAMP), 2-aminomethyl-I propanol (aminomethyl propanol) (AMP), and the like, or combinations thereof. The neutralizer, if present, may be provided in any amount, e.g., an amount sufficient to achieve a desired pH for the composition. In this respect, the composition preferably has a pH of from about 4-9, more preferably, from about 5-8, and still more preferably from about 5.5-7. Typically, the neutralizer may be present in an amount of from about 0.01%-10% by weight of the composition. In certain non-limiting embodiments, compositions of the invention may further comprise from about 0.0% to about 99.0% by weight of one or more alcohols. Alcohols that may be used according to the invention include fatty alcohols, such as cetyl alcohol, myristyl alcohol, stearyl alcohol, octyl alcohol, decyl alcohol, lauryl alcohol, and combinations thereof. Although one skilled in the art will appreciate that any alcohol suitable for use in the present invention may be used.

The improved composition of the present invention may also include from about 0.0% to about 99.0% by weight of one or more additional components without departing from the scope of the present invention. These components may include cosmeceuticals, anti-aging, rejuvenating or antioxidant therapies, antiinflammatory agents, as well as over-the-counter or prescription drugs, in various strengths as are known and pharmaceutically acceptable, depending on the desired ultimate formulation of the improved composition. It is further noted that the term "acid" includes pharmaceutically acceptable salts thereof.

The improved composition of the present invention may further include from about 0.0% to about 99.0% by weight of one or more non-active ingredients well known in the art including, for example, surfactants, preservatives, excipients, gelling agents, fragrances, buffers, binders, emulsifiers, solvents, electrolytes, sebum-absorbing polymers and other polymers, essential oils, botanical soothing agents, moisturizing beads or the like, silicone skin conditioning agents and emollients, sunblocking and sunscreening agents, physical exfoliating particles, stabilizers, liposomes and chelating agents. A preservative may be selected to kill bacteria that might otherwise be sustained or multiply in the composition. Preservatives suitable for this purpose are well known to those skilled in the art. In this respect, the type of preservative chosen will depend upon the components and the structure of the composition. For example, some preservatives are selected to combat microorganisms that are sustained in water, while others are selected to combat microorganisms that are sustained in oil. Illustrative of suitable preservatives include ethylparaben, propylparaben, methylparaben, EDTA or salts thereof (such as disodium EDTA), phenoxyethanol, DMDM hydantoin, and the like, or combinations thereof. Illustrative examples of suitable stabilizers include quaternary phosphates such as stearamidopropyl PG-dimonium chloride phosphate, linoleamidopropyl PG-dimonium chloride phosphate or cocamidopropyl PG-dimonium chloride phosphate. Suitable chelating agents include, but are not limited to, ethylenediamine tetracetic acid (EDTA) and derivatives and salts thereof, dihydroxyethyl glycine, citric acid, tartaric acid, and mixtures thereof.

Other suitable components may also include from about 0.0% to about 99.0% by weight of vitamins and/or amino acids including, but not limited to, water soluble vitamins (e.g., vitamin B1, B2, B6, B12, C); pantothenic acid, pantothenyl ethyl ether, panthenol, biotin, derivatives and combinations thereof; water-soluble amino acids such as asparagine, alanin, indole, glutamic acid, salts, derivatives and combinations thereof; water-insoluble vitamins such as vitamins A, D, and E, derivatives and combinations thereof; and water-insoluble amino acids such as tyrosine, tryptamine, salts, derivatives and combinations thereof. From about 0.0% to about 99.0% by weight of pigment materials may also be included in the composition of the present invention including, but not limited to, inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical and natural colors, and combinations thereof.

In an illustrative example, it has been determined that an effective combination of the improved composition comprises from about 0.01% to 90% purified water, from about 0.01% to 5.0% benzethonium chloride or benzalkonium chloride or mixtures thereof, from about 0.01% to 20% potassium hydroxide, from about 0.01% to 20% EDTA acid, from about 0.01% to 20% potassium chloride, from about 0.01% to 20% methylparaben, from about 0.01% to 20% propylparaben, from about 0.01% to 20% dimethicone, from about 0.01% to 20% distearyldimonium chloride, from about 0.01% to 20% cocamidopropyle PG-dimonium chloride phosphate, from about 0.01% to 20% glyceryl laurate, from about 0.01% to 20% behentrimonium methosulfate and cetyl alcohol, from about 0.01% to 20% steareth-21, and from about 0.01% to 20% cetyl alcohol.

The present invention is further illustrated by the following examples that are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

In an illustrative example, the composition of the present invention is created by first mixing together water and any solids (e.g., waxes) at elevated temperatures (e.g., from about 60-80° C.). Once the solids have completely melted, the mixture is cooled to ambient temperature. The remaining ingredients are added to cooled mixture and further mixed until blended and at the desired consistency.

Example 2

Using the method described in Example 1, an illustrative example of the inventive composition was prepared as shown in Table 1.

TABLE 1

An Illustrative Example of the Composition

| % (wt./wt.) | Trade Name | INCI Name |
|---|---|---|
| Part A | | |
| 81.71 | DI Water | water |
| 0.09 | Potassium Hydroxide | potassium hydroxide |
| 0.20 | Versene acid | EDTA acid |
| 0.50 | potassium chloride | potassium chloride |
| 0.20 | methylparaben | methylparaben |
| 0.10 | propylparaben | propylparaben |
| Part B | | |
| 3.00 | dimethicone | dimethicone |
| 3.50 | distearyldimonium chloride | distearyldimonium chloride |
| 2.00 | cocamidopropyl PG-dimonium chloride phosphate | cocamidopropyl PG-dimonium chloride phosphate |
| 1.00 | glyceryl laurate | glyceryl laurate |
| 2.00 | Incroquat Behenyl TMS-50 | behentrimonium methosulfate (and) cetyl alcohol |
| 0.50 | steareth-21 | steareth-21 |
| 4.00 | cetyl alcohol | cetyl alcohol |
| Part C | | |
| 1.00 | DI Water | water |
| 0.20 | benzethonium chloride | benzethonium chloride |
| 100.00 | | |

Example 3

In an illustrative example, the improved composition is applied topically to infected or soiled areas of the skin, such as hands, as often as necessary to sanitize and moisturize the skin. An effective amount of the composition for sanitizing and moisturizing the skin is applied to the skin and rubbed in Such effective amounts generally range from about 0.2 gm to about 2 gm and more preferably from about 0.3 gm to about 0.5 gm. This method for use on the skin comprises the steps of: a) applying an effective amount of the lotion to the skin, and b) rubbing the hands until absorbed. These steps can be repeated as many times as desired to achieve the desired moisturization and sanitization benefit. In accordance with the present invention, upon topical application of the composition to the skin, the composition preferably imparts long-lasting moisturization to the skin as measured by a moisture index. Several analytical methods and/or devices well known to those of ordinary skill in the art may be used to measure the moisture index.

Example 4

In an illustrative example, in-vitro analysis was performed on three embodiments of the composition of the present invention to evaluate the composition's anti-microbial activity. To better understand the anti-microbial performance of the embodiments, each embodiment was diluted to determine the concentration of product necessary to still remain effective. The following chart outlines the most dilute effective concentration for the 15 second microbe kill rate for each embodiment cross-referenced with each microbe tested:

TABLE 2

Test Strains.

| | Percent Reduction (15 sec) | Sanitizing Lotion (0.2% BZC) | Sanitizing Gel (62% (vol/vol) Ethanol) |
|---|---|---|---|
| Aerobic Organism: | | | |
| Staphylococcus aureus (MRSA) | >99.9 | >1:16 | <1:4 |
| Staphylococcus aureus | >99.9 | >1:16 | <1:4 |
| Streptococcus pneumoniae | >99.9 | >1:32 | <1:4 |
| Streptococcus pyogenes | >99.9 | >1:32 | <1:4 |
| Staphylococcus epidermidis | >99.9 | >1:32 | <1:4 |
| Enterococcus faecalis (MDR) | >99.9 | >1:16 | <1:4 |
| Escherichia coli | >99.9 | >1:4 | <1:4 |
| Pseudomonas aeruginosa | >99.9 | >1:4 | <1:4 |
| Klebsiella pneumoniae | >99.9 | >1:4 | <1:4 |
| Serratia marcescens | >99.9 | >1:4 | <1:4 |
| Burkholderia cepacia | >99.9 | <1:4 | <1:4 |
| Anaerobic Organism: | | | |
| Clostridium difficile (veg) | >99.9 | >1:16 | >1:4 |

Notes:
A) Due to resource constraints some tests were not diluted more than 1:4, 1:16 and/or 1:32
B) ">1:16" means that the 1:16 dilution sample showed complete (99.9%) kill at 15 seconds and that no greater dilutions were performed. Therefore the highest effective dilution can only be determined to be greater than 1:16
C) "<1:2" means that the 1:2 dilution sample didn't show complete kill at 15 seconds, but the lower dilution sample (e.g. 1:1) did. Therefore the highest effective dilution can only be determined to be less than 1:2.

Example 5

In another illustrative example, a ethanol-based antimicrobial composition (62% vol/vol ethanol solution, Batch # 288-031A) and one embodiment of the composition of the present invention (0.2% benzethonium chloride solution, Batch #288-031B) of the composition of the present invention were tested to demonstrate each embodiment's microbial reduction rate at zero time, 15 seconds, 30 seconds and 60 seconds against selected gram positive and gram negative aerobic bacteria, and Clostridium difficile as shown in Tables 2 and 3. This type of kill time assay is commonly used to evaluate new products and combination of agents and is well known in the art. Prior to performance of the kill time test, the MIC of each embodiment was determined for each organism by the standard MIC procedure. The MIC was then used as a guideline for kill time testing. Equipment used in shown in Table 4 and all growth and sterility control results conformed to Chattem's Quality Control guidelines. Identification of each inoculum strain was verified by Gram stain morphology, plate morphology and biochemical testing. The inoculum density was verified by duplicate plate counts. Equipment was monitored by temperature chart and documented daily, or when in use. A Quality Control sheet was used to record temperature, gas usage, and general chamber up keep when in use. The temperature on the ambient Precision incubator was also monitored and recorded daily.

Three MIC dilutions were tested for each test and reference solution. The final concentration was the average of the sum of the two plates, divided by two and multiplied by the dilution factor. The percent reduction was determined by comparing the final concentration result of the control to the test result. Certain protocol amendments were made as follows: Testing for C. difficile was added after the protocol was written. The same procedure written for the aerobes was used for the anaerobe with the exception of: a) C. difficile was grown and tested inside the anaerobic chamber; and b) Brucella agar was used for testing instead of Plate Count Agar. The anaerobic organism inoculum preparation for C. difficile required a denser turbidity, changing from 0.5 McFarland to 1.0 McFarland standard, to obtain proper recovery. Anaerobic bacteria normally require to be incubated for 48 hours to 72 hours. The plates from this organism were observed at 48 hours to 72 hours.

TABLE 2

Test Strains:

| Organism | Family/Genus representation: | ATCC # | Lot # | Expiration Date |
|---|---|---|---|---|
| Staphylococcus aureus (MRSA) | Staphylococci (MRSA) | 33592 | 651552 | 2009 Nov. 30 |
| Staphylococcus aureus | Staphylococci | 6538 | 66359 | 2009 Nov. 30 |
| Streptococcus pneumoniae | Streptococci | 6306 | 8044072 | 2009 Jul. 30 |
| Streptococcus pyogenes | Streptococci | 19615 | 8288053 | 2010 Mar. 29 |
| Staphylococcus epidermidis | Coagulase-negative Staphylococci | 12228 | 8038114 | 2009 Jul. 22 |
| Enterococcus faecalis (MDR) | Streptococci (MDR) | 51299 | 8196025 | 2009 Dec. 31 |
| Escherichia coli | Enterobacter | 8739 | 689085 | 2010 Feb. 28 |
| Pseudomonas aeruginosa | Proteobacteria | 9027 | 663587 | 2009 Nov. 30 |

TABLE 2-continued

| Organism | Family/Genus representation: | ATCC # | Lot # | Expiration Date |
|---|---|---|---|---|
| Klebsiella pneumoniae | Klebsiella | 31488 | 7242119 | 2009 Feb. 11 |
| Serratia marcescens | Enterobacter | 14756 | 8044086 | 2009 Jul. 3 |
| Burkholderia cepacia | Burkholderia | 25608 | 8308030 | 2010 Apr. 19 |
| Anaerobic Organism: | | | | |
| Clostridium difficile | Clostridium | 9689 | 8056029 | 2009 Aug. 10 |

Aerobic Organisms:

TABLE 3

Test Population Control ($10^4$)

| Organism | GBU F # 281-048 Test Population Control CFU/mL (Log 10) | GBU F # 281-069 Test Population Control CFU/mL (Log 10) |
|---|---|---|
| Staphylococcus aureus (MRSA) | 2.38 | 3.065 |
| Staphylococcus aureus | 2.14 | 30.54 |
| Streptococcus pneumoniae | 2.18 | 1.139 |
| Streptococcus pyogenes | 6.605 | 7.49 |
| Staphylococcus epidermidis | 3.995 | 3.36 |
| Enterococcus faecalis (MDR) | 1.31 | 14.99 |
| Escherichia coli | 8.8 | 3.89 |
| Pseudomonas aeruginosa | 12.14 | 3.07 |
| Klebsiella pneumoniae | 12.1 | 6.25 |
| Serratia marcescens | 5.4725 | 10.5 |
| Burkholderia cepacia | 1.48 | 3.625 |
| Anaerobic Organism: | | |
| Clostridium difficile | 3.66 | 4.1 |

TABLE 4

Study Materials:

| Culture Media | Supplies | Equipment |
|---|---|---|
| Blood agar (BA) | Petri dishes | Precision incubator |
| Mueller-Hinton broth (MHB) | 250 ml flasks if needed | Labconco class II Biosafety cabinet |
| Sterile 0.85% NaCl or Butterfield buffer | 20 ml test tubes (sterile) | Ohaus balance |
| Brucella agar | 0.5 McFarland turbidity standard | Autoclave |
| Tryptic soy broth (TSB) | 1.0 McFarland turbidity standard | Water bath |
| Standard methods agar (PCA) | Test tube rack | Bactron I anaerobic chamber |
| Chocolate agar | | |

Results. The MIC/Kill Time demonstrated microbial log reduction values over time. The test provided the opportunity to assess the speed at which bacterial kill may occur at a given concentration. The negative control was free of any growth. The positive control demonstrated proper growth and was free of contaminating organisms. The purity plates demonstrated a pure culture Having described the invention in detail, those skilled in the art will appreciate that modifications may be made of the invention without departing from the spirit and scope thereof. Therefore, it is not intended that the scope of the invention be limited to the specific embodiments described. Rather, it is intended that the appended claims and their equivalents determine the scope of the invention.

What is claimed is:

1. A moisturizing antimicrobial composition comprising:
   from about 0.05% to about 4.0% by weight of benzethonium chloride;
   from about 0.01% to about 10.0% by weight of a cationic surfactant having a molar mass of less than about 800 g/mol; and
   from about 30% to about 90% by weight of an aqueous carrier, wherein said composition is substantially free of ethanol.

2. The moisturizing composition of claim 1 wherein said composition comprises from about 0.1% to 0.5% by weight of benzethonium chloride.

3. The moisturizing composition of claim 1, wherein said cationic surfactant is a non-benzyl cationic surfactant.

4. The moisturizing composition of claim 3, wherein said non-benzyl cationic surfactant is a fatty quaternary amine selected from the group consisting of an alkyl ammonium chloride, alkyl ammonium methosulfate, derivatives and combinations thereof.

5. The moisturizing composition of claim 3, wherein said non-benzyl cationic surfactant is selected from the group consisting of behentrimonium methosulfate, distearyl dimonium chloride, derivatives and combinations thereof.

6. The composition of claim 1, wherein the composition has a form selected from the group consisting of emulsions, gels, sprays, and combinations thereof.

7. The composition of claim 1, further comprising from about 0.0001% to about 99.0% by weight of a component selected from the group consisting of anti-inflammatory agents, pharmaceuticals, and combinations thereof.

8. The composition of claim 1, wherein said composition has a viscosity of from about 10,000 to about 1,000,000 centipoise.

9. The composition of claim 1, wherein said composition is substantially free of polysorbates.

10. The composition of claim 1, wherein said composition is substantially free of anionic compounds.

11. A moisturizing antimicrobial composition comprising:
   from about 0.01% to 90% purified water;
   from about 0.01% to 5.0% of benzethonium chloride;
   from about 0.01% to 20% potassium hydroxide;
   from about 0.01% to 20% EDTA acid;
   from about 0.01% to 20% potassium chloride;
   from about 0.01% to 20% methylparaben;
   from about 0.01% to 20% propylparaben;
   from about 0.01% to 20% dimethicone;
   from about 0.01% to 20% distearyldimonium chloride;
   from about 0.01% to 20% cocamidopropyle PG-dimonium chloride phosphate;
   from about 0.01% to 20% glyceryl laurate;
   from about 0.01% to 20% behentrimonium methosulfate and cetyl alcohol;
   from about 0.01% to 20% steareth-21; and
   from about 0.01% to 20% cetyl alcohol.

12. A moisturizing antimicrobial composition comprising:

from about 0.05% to about 4.0% by weight of benzethonium chloride;

from about 0.01% to about 10.0% by weight of a cationic surfactant having a molar mass of greater than about 800 g/mol; and from about 30% to about 90% by weight of an aqueous carrier, wherein said composition is substantially free of ethanol, and wherein said cationic surfactant is a polyacrylate-1 crosspolymer.

* * * * *